US009585932B2

(12) United States Patent
Lu et al.

(10) Patent No.: US 9,585,932 B2
(45) Date of Patent: Mar. 7, 2017

(54) USE OF EPO-DERIVED PEPTIDE FRAGMENTS FOR THE TREATMENT OF NEURODEGENERATIVE DISORDERS

(71) Applicant: Peter C. Dowling, Fort Lee, NJ (US)

(72) Inventors: Wei Lu, Sea Girt, NJ (US); Peter C. Dowling, Ft. Lee, NJ (US); Rui Rong Yuan, Ft. Lee, NJ (US)

(73) Assignee: Peter C. Dowling, Fort Lee, NJ (US)

(*) Notice: Subject to any disclaimer, the term of this patent is extended or adjusted under 35 U.S.C. 154(b) by 105 days.

(21) Appl. No.: 13/792,336

(22) Filed: Mar. 11, 2013

(65) Prior Publication Data

US 2014/0256629 A1 Sep. 11, 2014
US 2016/0271206 A9 Sep. 22, 2016

Related U.S. Application Data

(63) Continuation-in-part of application No. 11/913,038, filed as application No. PCT/IB2006/003581 on May 1, 2006, now Pat. No. 8,653,028.

(60) Provisional application No. 60/676,592, filed on Apr. 29, 2005.

(51) Int. Cl.
| | |
|---|---|
| A61K 38/00 | (2006.01) |
| C07K 14/505 | (2006.01) |
| A61K 38/10 | (2006.01) |
| A61K 38/18 | (2006.01) |

(52) U.S. Cl.
CPC .......... *A61K 38/10* (2013.01); *A61K 38/1816* (2013.01); *C07K 14/505* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell | |
| 4,778,054 A | 10/1988 | Newell | |
| 4,811,731 A | 3/1989 | Newell | |
| 5,035,237 A | 7/1991 | Newell | |
| 5,986,047 A | 11/1999 | Wrighton | |
| 6,531,121 B2 | 3/2003 | Brines | |
| 6,831,060 B2 | 12/2004 | DeSauvage | |
| 6,849,602 B1 | 2/2005 | O'Brien | |
| 6,921,527 B2 | 7/2005 | Platz | |
| 7,211,253 B1 | 5/2007 | Way | |
| 7,410,941 B1 | 8/2008 | Brines | |
| 2004/0121958 A1 | 6/2004 | O'Brien | |
| 2004/0171123 A1 | 9/2004 | Rosen | |
| 2007/0184519 A1 | 8/2007 | Tangri | |
| 2009/0221482 A1* | 9/2009 | Cerami et al. | 514/12 |
| 2009/0258821 A1 | 10/2009 | Cerami | |
| 2011/0263504 A1 | 10/2011 | Cerami | |

FOREIGN PATENT DOCUMENTS

| | | |
|---|---|---|
| WO | WO 91/16038 A1 | 10/1991 |
| WO | WO 2004/108667 A2 | 12/2004 |

OTHER PUBLICATIONS

Supreme Court 2016 "Rapid Litigation Management Ltd v. Cellzdirect, Inc".*
Wang 2016 "Beneficial effect of erythropoietin short peptide on acute traumatic brain injury" neurotherapies 13:418-427.*
Abdul-Majid, et al., Comparing the pathogenesis of experimental autoimmune encephalomyelitis in CD4-/- and CD8-/- DBA/1 mice defines qualitative roles of different T cell subsets, J. Neuroimmunol. 141, pp. 10-19 (2003).
Battistini et al., CD8+ T cells from patients with acute multiple sclerosis display selective increase of adhesiveness in brain venules: a critical role for P-selectin glycoprotein ligand-1, Blood 101, pp. 2775-2782 (2003).
Bebo et al., Low-Dose Estrogen Therapy Ameliorates Experimental Autoimmune Encephalomyelitis in Two Different Inbred Mouse Strains, J. Immunol. 166, pp. 2080-2089 (2001).
Bernard et al., Myelin oligodendrite glycoprotein: a novel candidate authoantigen in multiple sclerosis, J. Mol. Med. 75, pp. 77-88 (1997).
Bettelli et al., Myelin Oligodendrocyte Glycoprotein-specific T Cell Receptor Transgenic Mice Development Spotaneious Autoimmune Optic Neuritis, J. Exp. Med. 197, pp. 1073-1081 (2003).
Belayev et al., Milddle cerebral artery occlusion in the mouse by intraluminal suture coated with poly-L-lysine: neurological and histological validation, Brain Res. 8933, pp. 181-190 (1999).
Brines, et al., Erythropoietin crosses the blood-brain barrier to protect against experimental brain injury, Proc. Nat'l. Acad. Sci. USA 97, pp. 10526-10531 (2000).
Brines, et al., Erythropoietin mediates tissue protectioh through an erythropoietin and common Beta-subunit heteroreceptor, Proc. Nat'l. Acad. Sci. USA 101, 14907-12 (2004).
Brines, et al., Emerging biological roles for erythropoietin in the nervous system, Nature Reviews (Neuroscience) 6, pp. 484-494 (2005).
Buemi et al., The Pleiotropic Effects of Erythropoietin in the Central Nervous System, Neuropathol. Ex. Neurol. 62, pp. 228-236 (2003).
Buemi et al., Erythropoietin and the brain: from neurodevelopment to neuroprotection, Clin. Sci (Lond.) 103, pp. 275-282 (2002).
Campana et al., Identification of a neurotrophic sequence in erythropoietin, Inn J. Mol. Med. 1, pp. 235-241 (1998).
Crawford et al., High prevalance of autoreactive, neuroantigen-specific CD8+ T cells in multiple sclerosis revealed by novel flow cytometric assay, Blood 103(11), pp. 4222-4231 (2004).
Engesser-Cesar et al., Voluntary Wheel Running Improves Recovery from a Moderate Spinal Cord Injury, J. Neurotrama 22, pp. 151-171 (2005).
Erbayraktar et al., Asialoerythropoietin is a nonerythropoietic cytokine with broad neuroprotective activity in vivo, Proc. Nat'l. Acad. Sci. USA 100, pp. 6741-6746 (2003).

(Continued)

*Primary Examiner* — Adam M Weidner
(74) *Attorney, Agent, or Firm* — Bryan D. Zerhusen; Locke Lord LLP

(57) ABSTRACT

The described invention provides methods and kits for administering an EPO-derived peptide to a subject suffering from a neurodegenerative disease. The EPO-derived peptide delays the onset and/or progression of a neurodegenerative disease, limits cognitive impairment in, and prolongs the survival of, subjects suffering from a neurodegenerative disease.

2 Claims, 8 Drawing Sheets

(56) References Cited

OTHER PUBLICATIONS

Farooq et al. The in vivo and in vitro induction of anterior chamber associated immune deviation to myelin antigens in C57BL/6 mice. Brian, Behavior, and Immunity. 42: 118-122 (2014).
Ghosh et al., Transdermal & Tropical Drug Delivery Systems 249-97 (1997).
Habek et al. Pathology of Acute Disseminated Encephalomyelitis. Translational Neuroscience 2(3) 252-255 (2011).
Kirsch et al. EMBO J. BMP-2 antagonists emerge form alterations in the low affinity binding epitope for receptor BMPR-II. vol. 19(13): 3314-3324 (2000).
Leist et al., Derivatives of Erythropoietin That Are Tissue Protective But Not Erythropoietic, Science 305, pp. 239-242 (2004).
Li et al., Beneficial Effect of Erythropoietin on Experimental Allergic Encephalomyelitis, Ann. Neurol. 56. pp. 767-777 (2004).
Livnha, et al., Functional Mimicry of a Protein Hormone by a Peptide Agonist: The ERO Receptor Complex at 2.8 Angstroms, Science 273, pp. 464-471 (1996).
McColl, et al., Extension of cerebral hypopertusion and ischaemic pathology beyond MCA territory after intraluminal filament occlusion in C5761/6J mice, Brain Res. 997, pp. 14-22 (2004).
Mun, et al., Impaired Biological Activity of Erythropoietin Cyanate Carbamylation, Blood Purif. 18, pp. 13-17 (2000).
Ngo et al. Computational Complexity, Protein Structure Prediction and the Levinthal Paradox. The Protein Folding Problem and Tertiary Strucutre Prediction, pp. 433-440 and 492-495 (1994).
Sakanaka et al., In vivo evidence that erythropoietin protects neurons from ischemic damage, Proc. Nat'l Acad. Sci. USA 95 pp. 4635-4640 (1988).
Scheff, et al., Experimental Modeling of Spinal Cord Injury: Characterization of a Force-Defined Injury Device, J. Neurotrama 20, pp. 179-193 (2003).
Schindler et al., Transcriptional Responses to Polypeptide Ligands: The JAK STAT Pathway, Ann. Rev. Biochem. 64, pp. 621-651 (1995).
Siren et al., Erythropoietin—a novel concept for neuroprotection, Eur. Arch. Psychiatry Clin. Neurosci. 251, pp. 179-184 (2001).
Sobel et al., The Immunopathology of Chronic Experimental Allergic Encephalomyelitis Induced in Rabbits with Bovine Proteolipid Protein, J. Immunol. 136, pp. 157-163 (1986).
Trapp, et al., Pathogenesis of tissue injury in MS lesions, J. Neuroimmunol. 98. pp. 49-56 (1999).
Tsai et al., A Critical Role of Erythropoietin Receptor in Neurogenesis and Post-Stroke Recovery, J. Neurosci. 26, pp. 1269-1274 (2006).
Tuohy et al., Identification of an Encephalitogenic Determinant of Myelin Proteolipid Protein for SJL Mice, J. Immunol. 142, pp. 1523-1527 (1989).
Watowich et al., Activation and Inhibition of Erythropoietin Receptor Function: Role of Receptor Dimerization, Mol. Cell Biol. 14, 3535-49 (1994).
Wells, J.A. Additivity of Mutational Effects in Proteins. Biochemistry, vol. 29, No. 37, pp. 8509-8517 (Sep. 18, 1990).
Wen, Erythropoietin Structure-Function Realtionships, J. Biol. Chem. 269, pp. 22839-22846 (1994).
Wrighton, et al., Small Peptides as Potent Mimetics of the Protein Hormone Erythropoietin, Science 273, pp. 458-463 (1996).
Yoshimura et al., Chronic Experimental Allergic Encephalomyelitis in Guinea Pigs Induced by Proteolipid Protein, J. Neurol. Sci. 69, pp. 47-58 (1985).

* cited by examiner

USE OF EPO-DERIVED PEPTIDE FRAGMENTS FOR THE TREATMENT OF NEURODEGENERATIVE DISORDERS

CROSS-REFERENCE TO RELATED APPLICATIONS

This application claims priority under 35 U.S.C. 120 from U.S. patent application Ser. No. 11/913,038 filed Aug. 18, 2008 now U.S. Pat. No. 8,653,028; which claims the benefit under 35 U.S.C. 119(e) of U.S. Provisional Patent Application 60/676,592 filed Apr. 29, 2005, and from U.S. provisional patent application Ser. No. 61/755,639, filed Jan. 23, 2013, the entire disclosures of which are incorporated herein by reference.

STATEMENT OF GOVERNMENT FUNDING

This invention was made with government support under Veteran Administration merit review. The government has certain rights in the invention.

FIELD OF INVENTION

The described invention generally relates to methods for delaying the onset and/or progression of a neurodegenerative disease and for prolonging survival in patients suffering from neurodegenerative diseases.

BACKGROUND OF THE INVENTION

Alzheimer's disease (AD) is a complex, heterogeneous, progressive neurodegenerative disease and is the most common form of dementia with prevalence estimates ranging from 14% at age 65 or older to more than 40% at age 85 or older (Changing the Trajectory of Alzheimers Disease: A National Imperative. Alzheimer's Association 2010; 2012 Alzheimer's Disease Facts and Figures. Alzheimer's Association 2012). In 2010, the Alzheimer's Association estimated that 35.6 million people worldwide would be living with a diagnosis of dementia and that the number of diagnosed dementia patients would nearly double every 20 years, leading to 65.7 million patients by 2030. This number indicates that dementia is rapidly becoming a major threat to healthcare. According to the Alzheimer's Association, delaying the onset of dementia by only a 5-year interval would decrease U.S. healthcare cost for dementia by almost 50% (Changing the Trajectory of Alzheimers Disease: A National Imperative. Alzheimer's Association 2010; 2012 Alzheimer's Disease Facts and Figures. Alzheimer's Association 2012). In response to this increasing healthcare threat, ten (10) Phase III clinical trials have been completed in AD over the past ten (10) years. All ten (10) clinical trials resulted in treatment failures. To date, no good therapeutic options are available, nor is there a cure for AD.

Over the past decade, understanding of the pathogenesis of AD has rapidly increased. There include characteristic pathologic changes (e.g., Aβ plaques, neurofibrillary tangles, neuronal cell loss, etc.) and prominent activation of a microglial/astrocytic immune/inflammatory process in AD patient brains, as well as in AD animal models. These abnormalities in pathology and disordered immune activation have led to the hypothesis that certain inflammatory cytokine mediators may be driving the Alzheimer's disease process (Wyss-Coray T. et al., J. Inflammation in Alzheimer's Disease-A Brief Review of the Basic Science and Clinical Literature, Cold Spring Harbor Perspect. Med. 2012; 2(1):a006346; Glass, C. K. et al., Mechanisms Underlying Inflammation in Neurodegeneration, Cell, 2010, 140: 918-934; Zilka, N. et al., Who Fans the Flames of Alzheimer's Disease Brains? Misfolded Tau on the Crossroad of Neurodegenerative and Inflammatory Pathways, J. Neuroinflammation, 2012, 9: 47).

New information has implicated a flawed innate immune response in the development of late onset Alzheimer's disease (Wyss-Coray T. et al., J. Inflammation in Alzheimer's Disease-A Brief Review of the Basic Science and Clinical Literature, Cold Spring Harbor Perspect. Med. 2012; 2(1):a006346; Glass, C. K. et al., Mechanisms Underlying Inflammation in Neurodegeneration, Cell, 2010, 140: 918-934; Zilka, N. et al., Who Fans the Flames of Alzheimer's Disease Brains? Misfolded Tau on the Crossroad of Neurodegenerative and Inflammatory Pathways, J. Neuroinflammation, 2012, 9: 47). For example, Stefansson et al. described a new missense mutation (R47H) present in a gene coding for the triggering receptor expressed on myeloid-derived cells 2 (called TREM-2) (Jonsson, T. et al., N Engl. J. Med., 2013, 368: 107-116, DOI: 10.1056/NEJMoa1211103; Guerreiro, R. et al, N Engl. J. Med., 2012, DOI: 10.1056/NEJMoa1211851; Piccio, L. et al., Eur. J. Immuno., 2007, 37: 1290-1301; Neumann, H. et al., Neruoimmunol., 2007, 184: 92-99). TREM-2 is an innate immune receptor highly expressed on immature dendritic cells, microglia, and osteoclasts. It is involved in phagocytosis of neural debris in the brain and it concomitantly down-regulates pro-inflammatory cytokine production. Homozygous loss-of-function TREM-2 mutations have been previously linked to an early onset of dementia coupled with bone abnormalities. Stefansson et al. reported that the heterozygous TREM-2 missense genetic variant provoked a loss-of-function (i.e., impaired innate immune regulation). Such loss-of-function resulted in a failure to block pro-inflammatory cytokine production, which in turn, fueled rampant inflammation in the AD brain. In addition to a loss-of-function, Stefansson et al. reported that the TREM-2 missense genetic variant was associated with a significant increase in the risk of late onset Alzheimer's disease (See also, Jonsson, T. et al., N Engl. J. Med., 2013, 368: 107-116, DOI: 10.1056/NEJMoa1211103; Guerreiro, R. et al., N Engl. J. Med., 2013, 368: 117-127, DOI: 10.1056/NEJMoa1211851).

In addition to the work of Stefansson et al., another investigator, Relkin et al., who has treated small numbers of mild to moderate AD patients with pooled intravenous immunoglobulin (IVIG) as a possible immunotherapy (Relkin, N. et al., AAIC 2012: abstract P3-381), and reported that AD patients treated with IVIG showed a decreased rate of ventricular enlargement in association with a reduction in whole brain atrophy and less cognitive impairment compared to a group of AD patients treated with placebo (i.e., control group). Despite its potential as an AD therapy, insufficient supply of pooled IVIG on a worldwide basis making its use problematic.

Thus, the need exists to develop alternative sources of immune modifying agents to delay onset and/or progression of the neurodegenerative process in patients suffering from AD and other neurodegenerative diseases (Hughes, R. A. et al., Clin. and Exp. Immunol., 2009, 158 (Suppl. 1); 34-42).

Erythropoietin (EPO), a 165 amino acid glycoprotein hormone initially identified as a hematopoietic growth factor, has been used extensively for the treatment of anemia in humans. Recently, EPO has received considerable attention due to its potential neuroprotective capabilities following brain and central nervous system (CNS) injury (Yuan, R. et al., PLoS 2008 3:e1924; Brines, M. L. et al., Proc. Natl. Acad. Sci. USA, 97: 10526-31 (2000); Siren, A. L. and Ehrenreich, H., Eur. Arch. Psychiatry Clin. Neurosci., 251: 179-184 (2001); Buemi, M. et al., J. Neuropathol. Exp. Neurol., 62: 228-236 (2003); Li, W. et al., Ann. Neurol., 56: 767-777 (2004); Sakanaka, M. et al., Proc. Natl. Acad. Sci. USA, 95: 4635-4640 (1998)). Exogenously administered EPO has been shown to significantly reduce neurologic impairment in several diverse forms of neurologic injury (e.g., acute brain trauma, epilepsy, autoimmune model of demyelinating disease, etc.) (Brines, M. L. et al., Proc. Natl. Acad. Sci. USA, 97: 10526-31 (2000); Li, W. et al., Ann. Neurol., 56: 767-777 (2004); Tsai, P. T. et al., J. Neurosci., 26: 1269-1274 (2006); Buemi, M. et al., Clin. Sci. (Loud), 103: 275-282 (2002)). However, long-term EPO therapy remains significantly limited in non-anemic patients with neurological injury, because administration of EPO in these patients may overly stimulate erythropoiesis leading to serious side-effects such as heart attack and stroke. In order to overcome these serious side-effects, EPO therapy would have to be limited to short-term use, or alternatively, to the use of other EPO molecular preparations (e.g., fragments, mutants, etc.) devoid of hematopoietic effects. Indeed, molecular preparations such as an asialo-form of EPO, carbamylated EPO (CEPO) and certain EPO mutants have been shown to be neuroprotective in animals following experimental traumatic spinal cord injury or acute stroke without provoking an increase in red blood cell production (Erbayrakar, S. et al., Proc. Natl. Acad. Sci. USA, 100: 6741-6746 (2003); Leist, M. et al., Science, 305: 239-242 (2004); Mun, K. C. and Golpher, T. A., Blood Purif., 18: 13-17 (2000); Brines, M. et al., Proc. Natl. Acad. Sci. USA, 101: 14907-14912 (2004)). In addition, a seventeen (17) amino acid EPO-derived linear peptide was reported to have neuroprotective effects in vitro (Campana, W. M. et. al., Int'l J. Mol. Med., 1: 235-241 (1998)).

The present inventors have synthesized a library of short, stabilized EPO-derived peptides, which induce substantial neuroprotective immunomodulatory effects in acute murine models of human multiple sclerosis and acute traumatic brain injury (US 2009/0029906). These synthetic, short, stabilized peptides were derived from a distinct domain embedded within the early sequence of the EPO molecule. Whereas the full-length EPO molecule is manufactured by an expensive cell culture process based on CHO cells, the synthetic, short, stabilized EPO-derived peptides provide the advantage of low manufacturing costs, low immunogenicity, and high stability (US 2009/0029906; US 2011/0190217). Notably, these EPO-derived peptides are devoid of hematopoietic effects. A lead compound, JM4 (GCAEHC-SLNENITVPDTKV; SEQ ID NO: 1), a stabilized, cyclic peptide derived from the first loop of erythropoietin, has been evaluated in vitro and in vivo. To date, JM4 shows considerable promise as a potent immune/inflammatory modulator useful for treating animal experimental autoimmune encephalomyelitis (EAE) and for treating murine acute brain injury. JM4 shows good efficacy in animals and the preliminary side effect profile is highly favorable compared to whole molecule erythropoietin.

JM4 exhibits robust immunomodulation in several preclinical animal models, including EAE, brain trauma and collagen II induced autoimmune arthritis, but does not depress overall amounts of B- or T-cells, Instead, JM4 favorably modulates the ratio of T-suppressor (Treg) to T helper 17 (Th-17) effector cells. JM4 also strongly down-regulates antigen specific T-cell proliferation through its effect on dendritic cells or microglia (innate immunity). JM4 also blocks pro-inflammatory cytokine production. The medicinal attractiveness of these EPO-derived peptides is underscored by the observation that JM4 treated mice appear normal and lack any effects on hematopoiesis and blood chemistries.

In animal models of dementia, we have found EPO-derived peptides are capable of delaying the onset of disease and delaying progression of dementia and prolonging overall survival of subjects. Neurofibrillary tangles (NFTs) are aggregates of the microtubule-associated protein "tau", which have become hyperphosphorylated and accumulate inside the cells themselves. Tau is relatively abundant in neurons but is present in all nucleated cells and functions physiologically to bind microtubules and stabilize microtubule assembly for polymerization. In one of our models of neurodegenerative disease, the EPO-derived peptide prevented ventricular enlargement, blocked over-expression of tau protein and over-expression of major histocompatibility complex class II (MHC II) in microglial cells.

SUMMARY OF THE INVENTION

The present disclosure provides methods, compositions and kits useful in the treatment of neurodegenerative diseases, such as Alzheimer's disease.

According to one aspect, the described invention provides a method for delaying the onset or progression of disease in a subject suffering from a neurodegenerative disease comprising: (a) providing a composition comprising at least one isolated, synthetic or substantially pure EPO-derived peptide; and (b) administering to the subject a therapeutic amount of the composition such that the therapeutic amount is effective to delay onset or progression of the neurodegenerative disease.

According to another aspect, the described invention provides a method for limiting cognitive impairment in a subject suffering from a neurodegenerative disease comprising: (a) providing a composition comprising at least one isolated, synthetic or substantially pure EPO-derived peptide; and (b) administering to the subject a therapeutic amount of the composition such that the therapeutic amount is effective to delay onset or progression of the neurodegenerative disease, thereby limiting cognitive impairment in the subject.

According to another aspect, the described invention provides a method for prolonging survival of a subject suffering from a neurodegenerative disease comprising: (a) providing a composition comprising at least one isolated, synthetic or substantially pure EPO-derived peptide; and (b) administering to the subject a therapeutic amount of the composition such that the therapeutic amount is effective to delay onset or progression of the neurodegenerative disease, thereby prolonging survival of the subject.

According to one embodiment, the EPO-derived peptide is synthetic. According to another embodiment, the EPO-derived peptide is not hematopoietic. According to another embodiment, the EPO-derived peptide is cyclic. According to yet another embodiment, the EPO-derived peptide has the sequence GCAEHCSLNENITVPDTKV as set forth in SEQ ID NO: 1.

According to one embodiment, the neurodegenerative disease is Alzheimer's disease.

According to one embodiment, the route of administering the composition is selected from the group consisting of parenteral, oral, inhalation, insufflation, topical, buccal and rectal. According to another embodiment, the route of administering is parenteral.

According to another embodiment, the composition comprises a pharmaceutically acceptable excipient.

According to another aspect, the described invention provides a kit comprising a composition. The composition comprises at least one EPO-derived peptide; and a packaging material. According to one embodiment, the kit comprises an EPO-derived peptide that has the sequence GCAEHCSLNENITVPDTKV as set forth in SEQ ID NO: 1. According to another embodiment, the kit comprises a means for administering the EPO-derived peptide. According to another embodiment, the kit comprises a composition that comprises a pharmaceutically acceptable excipient. According to yet another embodiment, the kit comprises a packaging material that is an instruction.

DETAILED DESCRIPTION OF THE INVENTION

Figure 1:
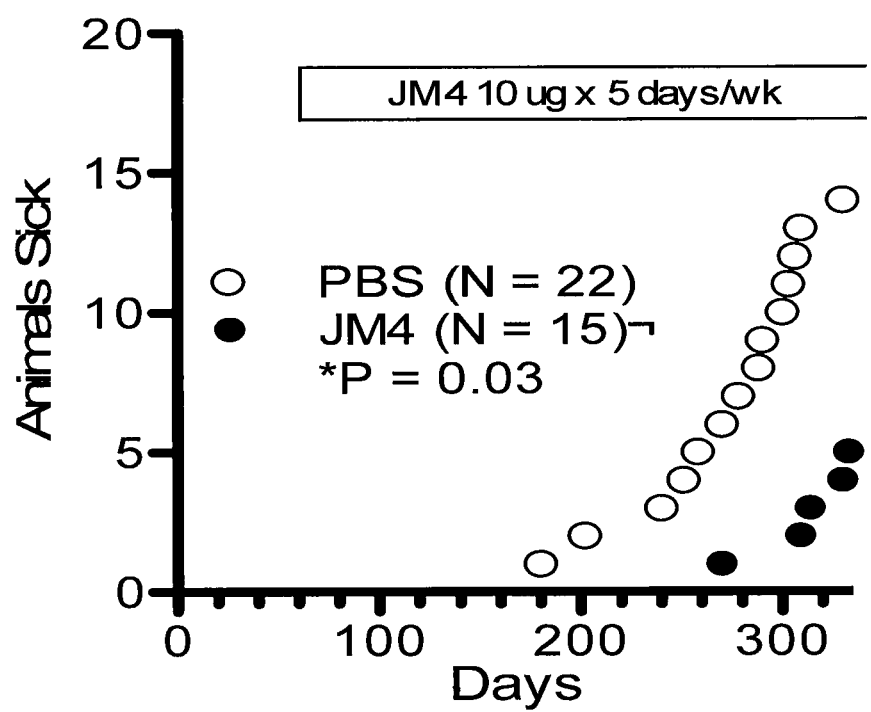
FIG. 1 depicts neurodegenerative tau mice treated with either JM4 peptide (closed circles) at 10 μg for 5 days per week (N=15) or with phosphate-buffered saline (PBS) (i.e., sham-treated) (open circles) (N=22) from the age of two (2) months. JM4 delayed the onset of disease and therefore allowed longer disease-free survival compared to sham-treated animals.

The present invention can be better understood from the following description of exemplary embodiments, taken in conjunction with the accompanying figures and drawings. It should be apparent to those skilled in the art that the described embodiments of the present invention provided herein are merely exemplary and illustrative and not limiting.

Definitions

Various terms used throughout this specification shall have the definitions set out herein.

The term "AD mice" as used herein, refers to mice, which are routinely used in Alzheimer's disease research, having the phenotype 129-Psen1$^{tm1Mpm}$ TG (APPSwe, tau P301L) 1Lfa/J. These transgenic mice are provided by Jackson Laboratory (Bar Harbor, Me.). These mice, which exhibit traits similar to those observed in Alzheimer's disease patients (e.g., plaque and tangle pathology associated with synaptic dysfunction), are homozygous for three mutant alleles: (i) Psen1; (ii) APPSwe; and (iii) P301L. The mutant alleles are overexpressed in the CNS, particularly in Alzheimer's disease-relevant areas (i.e., the hippocampus and cerebral cortex). Amyloid beta peptide deposits progressively increase, and intracellular immunoreactivity may be detected in some brain regions by three (3) to four (4) months or more. Synaptic transmission and long-term potentiation are demonstrably impaired by six (6) months. Aggregates of conformationally altered pathology may be detected in the hippocampus between twelve (12) to fifteen (15) months.

The term "administer", "administering" or "to administer" as used herein, refers to the giving or supplying of a medication, including in vivo administration, as well as administration directly to tissue ex vivo. Generally, compositions may be administered systemically either orally, bucally, parenterally, topically, by inhalation or insufflation (i.e., through the mouth or through the nose) or rectally in dosage unit formulations containing conventional nontoxic pharmaceutically acceptable carriers, adjuvants and vehicles as desired, or may be locally administered by means such as, but not limited to, injection, implantation, grafting, topical application or parenterally.

The terms "agent" and "therapeutic agent" are used interchangeably herein to refer to a drug, molecule, composition, or other substance that provides a therapeutic effect. The term "active agent" as used herein, refers to the ingredient, component or constituent of the compositions of the present invention responsible for the intended therapeutic effect.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide. The following represent groups of amino acids that are conservative substitutions for one another:

Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

The terms "amyloid peptide", "amyloid B peptide", and "AB" are used interchangeably herein to refer to the family of peptides generated through proteolytic processing of the amyloid precursor protein (APP).

The term "astrocyte" as used herein, refers to relatively large glial cells with thread-like projections that connect with neurons and small blood vessels (capillaries). These projections form part of the so-called "blood-brain barrier." Astrocytes also accumulate in areas where nerves have been damaged (astrocytosis), sealing off these areas. An excess of astrocytes in damaged areas of the CNS is known as gliosis.

The term "cellular immunity" as used herein, refers to T lymphocyte-mediated immunity. T lymphocytes, or T cells, are known to directly kill target cells, to provide "help" for such killers, to activate other immune system cells (e.g., macrophages), to help B cells make an antibody response, to downmodulate the activities of various immune system cells, and to secrete cytokines, chemokines, and other mediators. T cells are divided into two (2) major classes: T helper cells (Th) and regulatory T cells (Treg). T helper cells are further subdivided into T helper 1 (Th1) cells and T helper 2 (Th2) cells. The type 1 and type 2 helper classes are defined by their cytokine secretion profiles. T-helper 1 (Th1) cells, which are implicated in the stimulation of inflammation, produce IFN-gamma, GM-CSF, TNF-beta, and TNF alfa. TNF and IFN-gamma signals synergize in inducing an activated state in the macrophage, and lead to increased expression of adhesion and homing molecules in the vascular endothelium, which recruit additional blood-born leukocytes to the site of inflammation. (See, Paul, Fundamentals of Immunol. p. 397). T helper 2 (Th-2) cells produce IL-4, IL-5, IL-10, and IL-13, and provide help for B cells in their activation and differentiation leading to the humoral immune response. (de Waal Malefyt, Immunity 31: 700-702 (2009)). Regulatory T cells, either natural, induced, or Trl cells, produce IL-10 and TGFβ, suppress the activation of effector T cells, and provide a counter-balance against uncontrolled and harmful T cell responses. Id. Th9 cells may provide additional help for mast cells through the production of IL-9. Id. Th17, an additional T cell subset, produces IL-17A, 17-17F, IL-22 and CCL20, which act on stromal and epithelial cells to induce a number of secondary effector molecules, such as G-CSF, which stimulates the production and mobilization of neutrophils, acute phase proteins, chemokines, and antimicrobial peptides. Id. Naive T cells can differentiate into any of the distinct T cell subsets when activated in the presence of appropriate signals and cytokines. The induction of a maturation process in dendritic cells is a crucial step for efficient priming of naive T cells. There is an extensive cross-regulation between subsets to ensure that the appropriate T cell subset is activated. Id.

The term "central nervous system" or "CNS" as used herein, refers to the brain and spinal cord.

The term "cognitive function" as used herein, refers to the intellectual processes resulting in an understanding, perception or awareness of one's ideas as well as the ability to perform mental tasks, such as thinking, learning, judging, remembering, computing, controlling motor functions and the like. Progressive cognitive disease or impairment of cognitive function is usually diagnosed clinically from patient history, collateral history from relatives, and clinical observations, based on the presence of characteristic neurological and neuropsychological features and the absence of alternative conditions. These criteria require that the presence of cognitive impairment, and a suspected dementia syndrome, be confirmed by neuropsychological testing. Advanced medical imaging with computed tomography (CT) or magnetic resonance imaging (MRI), and with single photon emission computed tomography (SPECT) or positron emission tomography (PET) may be used to help exclude other cerebral pathology or subtypes of dementia. Assessment of intellectual functioning including memory testing can further characterize the state of the disease. A histopathologic confirmation including a microscopic examination of brain tissue may be required for a definitive diagnosis. For AD, eight cognitive domains are most commonly impaired: memory, language, perceptual skills, attention, constructive abilities, orientation, problem solving and functional abilities. These domains are equivalent to the NINCDS-ARDA Alzheimer's Criteria as listed in the *Diagnostic and Statistical Manual of Mental Disorders* (DSM-IV-TR) published by the American Psychiatric Association.

The term "condition" as used herein, refers to a variety of health states and is meant to include disorders or diseases caused by injury or any underlying mechanism or disorder.

The term "cyclic" as used herein, refers to an amino acid sequence that comprises, at least in part, a closed chain. For example, oxidation-reduction of two sulfur-containing amino acids (e.g., cysteine and methionine) located within a suitable bond-forming distance n a given peptide sequence may, under the appropriate conditions, lead the sulfur moieties to form a disulfide (S—S) bridge, which comprises a strong covalent disulfide bond between the sulfhydral groups of these amino acids. According to the described invention, the amino acid sequence of some of the EPO-derived peptides of the described invention contain two cysteines located within a suitable bond-forming distance. Oxidation-reduction of the sulfide groups on each of these cysteines results in the formation of a disulfide bond.

The term "cytokine" as used herein, refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines The term "delay", "delaying", "delayed" or "to delay" as used herein, refers to stopping, detaining or hindering for a time; to cause to be slower or to occur more slowly than normal.

The term "dementia" as used herein, refers to a decline or a progressive decline in cognitive function due to damage or disease in the brain beyond what might be expected from normal aging.

The term "derivative" as used herein, refers to a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as alkylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well known chemical modification methods (see, e.g., Glazer et al., Chemical Modification of Proteins, Selected Methods and Analytical Procedures, Elsevier Biomedical Press, New York (1975)). For example, according to the present invention, the term includes an amino acid sequence produced from an EPO peptide either directly or by modification or partial substitution of the EPO peptide.

The term "disease" or "disorder" as used herein, refers to an impairment of health or a condition of abnormal functioning. By way of example, patients suffering from Alzheimer's disease often suffer from such symptoms as memory loss, agitation and mood swings, impaired judgment, difficulty performing familiar tasks, trouble planning or problem-solving, misplacing objects, confusion with time and/or place, difficulty communicating, wandering, repetitive speech or actions, difficulty with visual and/or spatial relationships, purposeless activity, social withdrawal, loss of initiative and motivation, failure to recognize family members, loss of motor skills and sense of touch, difficulty dressing, disregard for grooming and hygiene, inappropriate behavior, delusions and paranoia, verbal and/or physical aggression, difficulty sleeping and childlike behavior.

The terms "erythropoietin", "EPO", "whole molecule erythropoietin", "whole molecule EPO", "whole erythropoieting", "whole EPO", "whole erythoropoietin molecule", "whole EPO molecule", "full-length erythropoietin" and "full-length EPO" are used interchangeably herein to refer to the 165 amino acid glycoprotein hormone erythropoietin.

The term "EPO-derived peptide" as used herein, refers to a stabilized short peptide derived from whole molecule EPO according to the present invention. This term includes, but is not limited to, JM4 peptide, whose N-terminal to C-terminal amino acid sequence is GCAEHCSLNENITVPDTKV (SEQ ID NO: 1).

The term "glial cell" as used herein, refers to the connective tissue cells of the CNS that serve as the supportive structure that holds together and protects neurons.

The term "glial filament acidic protein" or "GFAP" as used herein, refers to intermediate filament protein predominantly expressed in cells of astroglial origin, which is a marker for astrocytes.

The terms "immune response" and "immune-mediated" are used interchangeably herein to refer to any functional expression of a subject's immune system, against either foreign or self antigens, whether the consequences of these reactions are beneficial or harmful to the subject.

The terms "immunomodulating", "immune modulating", "immunomodulation", "immune modulation", "immunomodulate" and "immune modulate" are used interchangeably herein to refer to changes in the body's immune system, caused by agents that activate or suppress its function.

The term "injury" as used herein, refers to damage or harm to a structure or function of the body caused by an outside agent or force, which may be physical or chemical.

The term "isolated molecule" as used herein, refers to a molecule that is substantially pure and is free of other substances with which it is ordinarily found in nature or in vivo systems to an extent practical and appropriate for its intended use. For example, the compositions are sufficiently pure and are sufficiently free from other biological constituents of host cells so as to be useful in, for example, producing pharmaceutical preparations or sequencing.

The term "major histocompatibility complex" or "MHC" as used herein refers to a complex of vertebrate genes coding for a large family of cell-surface proteins that bind peptide fragments of foreign proteins and present them to T-lymphocytes to induce an immune response. The MHC also plays a role in resistance to infection and in susceptibility to a number of autoimmune diseases. The MHC complex is divided into three subgroups: MHC class I (MHC I); MHC class II (MHC II); and MHC class III (MHC III). MHC I molecules are present on nearly every nucleated cell of the body. MHC I presents peptides derived from cytosolic proteins and/or peptides from infectious agents. MHC II molecules are found only on specialized, antigen-presenting cell types such as macrophages, dendritic cells, activated T cells and B cells. MHC II presents peptides derived from extracellular proteins that are internalized by the cell from its environment, digested by lysosomes and bound by MHC II before its migration to the plasma membrane. MHC II interacts with helper (CD4+) T cells to trigger an appropriate immune response. MHC III molecules include several secreted proteins comprising components of the complement system (e.g., C2, C and B factor), cytokines (e.g., TNF-$\alpha$, LTA and LTB) and heat shock proteins (hsp).

The term "microglia" as used herein, refers to the smallest of the glial cells that can act as phagocytic cells, cleaning CNS debris. Microglia are considered to be a type of immune cell found in the brain and are closely related to other phagocytic cells including macrophages and dendritic cells. Microglia are derived from myeloid progenitor cells from bone marrow. During embryonic development, myeloid progenitor cells migrate to the CNS where they differentiate into microglia.

The term "mimic" as used herein, refers to an EPO derivative comprising a functional domain of EPO protein and a stabilizing domain of EPO protein, alone or in combination with, another molecule which will produce a biological effect, such as immunomodulation.

The term "modulate" as used herein, refers to the regulation, alteration, adaptation or adjustment to a certain measure or proportion.

The term "neurological injury" as used herein, refers to an injury of, or pertaining to, or relating to the nerves and the nervous system comprising the CNS and peripheral nervous system.

The term "neurodegenerative disease" as used herein, refers to a clinical syndrome that involves loss of memory and cognitive impairments of sufficient severity to interfere with social or occupational functioning. A neurodegenerative disease is characterized by at least two (2) abnormalities: memory loss in an otherwise alert patient and impairments in at least one other area of cognition-language, problem solving, judgment, calculation, attention, perception, praxis and the like. Alzheimer's disease is a prototypical neurodegenerative disease that is characterized by a series of abnormalities in the brain that selectively affect neurons in specific regions, particularly in the neocortex, the entorhinal area, hippocampus, amygdala, nucleus basalis, anterior thalmus, and serveral brain stem monoaminergic nuclei (See, Principles of Neural Science, Fourth Edition, Edited by Eric R. Kandel, James H. Schwartz and Thomas M. Jessell, McGraw-Hill Health Professions Division, 2000).

The term "neurofibrillary tangles" or "NFT" as used herein, refers to aggregates of the microtubule-associated protein tau, which have become hyperphosphorylated and accumulate inside the cells themselves. The presence of NFT is a characteristic of AD brains. These aggregations of hyperphosphorylated tau protein also are referred to as "paired helical filaments" (PHF). The role of PHF, whether as a primary causative factor in AD or in a more peripheral role, is uncertain. However, the accumulation of PHF cause the destabilization of the microtubule network, thus compromising neuronal scaffolding, and disrupting cellular trafficking and signal transduction/communication, and leading to neuronal death.

The term "parenteral" as used herein, refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersion or wetting agents and suspending agents.

The term "pathology" as used herein, refers to the nature of a disease or condition, especially changes in body tissues and organs that cause or are caused by a disease or condition. For example, Alzheimer's disease pathology includes, but is not limited to, accumulation and aggregation of amyloid plaques, hyperphosyphorylation of tau protein, neurofibrillary tangle formation, inflammatory responses such as microglial activation and cytokine release, astrocytosis, acute protein release, over-expression of major histocompatibility complex class II (MHC II) and the like, oxidative injury, ventricular enlargement, neuronal/neuritic dysfunction and death in the hippocampus and cerebral cortex, progressive neurotreansmitter deficits, synaptic loss and shrinkage of neuronal perikarya.

The term "peptide" as used herein, refers to a molecule of two or more amino acid chemically linked together. A peptide may refer to a polypeptide, protein or peptidomimetic. The peptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the peptides can have peptidomimetic bonds, such as ester bonds, to prepare peptides with novel properties. For example, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a peptide would be resistant to protease activity, and would possess an extended half-live in vivo. Accordingly, these terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The term "peptide" is also inclusive of modifications including, but not limited to, glycosylation, lipid attachment, sulfation, gamma-carboxylation of glutamic acid residues, hydroxylation and ADP-ribosylation. In some embodiments, the peptide is of any length or size. Use herein of the terms "peptide", "peptides", or "peptidomimetic" should be taken to include reference to "derivatives" of such compounds, unless the context requires otherwise, and to include "prodrugs."

The term "peptidomimetic" as used herein refers to a small protein-like chain designed to mimic a peptide. A peptidomimetic typically arises from modification of an existing peptide in order to alter the molecule's properties.

The term "peripheral nervous system" or "PNS" as used herein, refers to the nerves and ganglia outside of the brain and spinal cord. The main function of the PNS is to connect the CNS to the limbs and organs.

The term "prevent", "preventing", "prevented" or "to prevent" as used herein, refers to effectual stoppage of action or progress.

The term "prolong", "prolonging", "prolonged" or "to prolong" as used herein, refers to lengthening in time, extent, scope or range.

The term "reduce", "reducing", "reduced" or "to reduce" as used herein, refers to a diminishing, a decrease in, an attenuation or abatement of the degree, intensity, extent, size, amount, density or number of The term "syndrome" as used herein, refers to a pattern of symptoms indicative of some disease or condition.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA,* 1989, 89:10915).

In addition to calculating percent sequence identity, the BLAST algorithm also performs a statistical analysis of the similarity between two sequences (see, e.g., Karlin & Altschul, *Proc. Natl. Acad. Sci. USA,* 1993, 90: 5873-5787). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.,* 1993, 17:149-163) and XNU (Clayerie and States, *Comput. Chem.,* 1993, 17:191-201) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 1988, 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The terms "subject" and "patient" are used interchangeably herein to refer to animal species of mammalian origin that may benefit from the administration of a drug composition or method of the described invention. Examples of subjects include humans, and other animals such as horses, pigs, cattle, dogs, cats, rabbits, mice, rats and aquatic mammals.

The term "tau mice" as used herein, refers to a C3-Tg (Prmp-MAPT*P301S) PS19Vle/J Tauopathy mouse (Jackson Laboratory).

The terms "therapeutic amount", "therapeutically effective amount" and "amount effective" are used interchangeably herein to refer to an amount of one or more active agent(s) that is sufficient to provide the intended benefit of treatment. Dosage levels are based on a variety of factors, including the type of injury, the age, sex, weight, medical condition of the patient, the severity of the condition, the route of administration and the particular active agent employed. The dosage regimen may vary widely, but can be determined routinely by a physician using standard methods.

The term "treat", "treating" or "to treat" as used herein, refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously asymptomatic for the disorder. The term "treat", "treating" or "to treat" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms.

The term "variant" as used herein refers to a peptide sequence that varies at one or more amino acid positions with respect to the reference peptide. A variant can be a naturally-occurring variant or can be the result of spontaneous, induced, or genetically engineered mutation(s) to the nucleic acid molecule encoding the variant peptide. A variant peptide can also be a chemically synthesized variant. A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan.

The present disclosure provides methods, compositions and kits useful in the treatment of neurodegenerative diseases, such as Alzheimer's disease.

According to one aspect, the described invention provides a method for delaying the onset or progression of a neurodegenerative disease. It is well understood that the onset or progression of a neurodegenerative disease is routinely determined, for example, by cognitive assessment, neuroimaging techniques and/or biomarker detection.

Examples of cognitive assessments used to determine the onset or progression of a neurodegenerative disease include, but are not limited to, memory loss, agitation and mood swings, impaired judgment, difficulty performing familiar tasks, trouble planning or problem-solving, misplacing objects, confusion with time and/or place, difficulty communicating, wandering, repetitive speech or actions, difficulty with visual and/or spatial relationships, purposeless activity, social withdrawal, loss of initiative and motivation, failure to recognize family members, loss of motor skills and sense of touch, difficulty dressing, disregard for grooming and hygiene, inappropriate behavior, delusions and paranoia, verbal and/or physical aggression, difficulty sleeping and childlike behavior.

Exemplary neuroimaging techniques used to determine the onset or progression of a neurodegenerative disease include, but are not limited to, computed tomography (CT), magnetic resonance imaging (MRI), single photon emission computed tomography (SPECT), diffusion tensor imaging, positron emission tomography (PET) and multiphoton microscopy. Typically, one will use radiopharmaceuticals, tracers, fluorophores, and the like, in combination with neuroimaging techniques. For example, Pittsburgh compound B ([N-Methyl-$^{11}$C]$_2$-(4'-methylamiophenyl)-6-hydroxybenzothiazole) (PiB) or florbetapir ($^{18}$F) ((E)-4-(2-(6-(2-(2-(2-([18F]-fluoroethoxy)ethoxy)ethoxy)pyridin-3-yl)vinyl)-N-methyl benzenamine) ($^{18}$F-AV-45) may be used in combination with PET to detect β-amyloid (Aβ) deposits in the brain. Exemplary fluorophores typically used in combination with multiphoton microscopy to detect Aβ deposits in the brain include Thioflavin S and Thioflavine T derivative.

It is understood that biomarkers may also be used to determine the onset or progression of a neurodegenerative disease. Possible sources of biomarkers include cerebrospinal fluid (CSF) and plasma. Exemplary CSF biomarkers include, but are not limited to, Aβ 42, T-tau and P-tau peptides as well as presenilin-I gene mutations and apoE4 allele. Non-limiting examples of plasma biomarkers include Aβ 40 and Aβ 42 peptides. Detection of biomarkers may be accomplished by techniques known in the art, such as, without limitation, enzyme-linked immunosorbent assay (ELISA), Western blot, polymerase chain reaction (PCR), reverse transcription-polymerase chain reaction (RT-PCR), and the like.

According to another aspect, the described invention provides a method for limiting cognitive impairment in a subject suffering from a neurodegenerative disease. It is understood that cognitive disease or impairment of cognitive function is usually diagnosed clinically from patient history, collateral history from relatives, and clinical observations, based on the presence of characteristic neurological and neuropsychological features and the absence of alternative conditions. Advanced medical imaging such as computed tomography (CT) or magnetic resonance imaging (MRI), and with single photon emission computed tomography (SPECT) or positron emission tomography (PET) may be used to help exclude other cerebral pathology or subtypes of dementia. Assessment of intellectual functioning including memory testing may further characterize the state of the disease. Histopathologic confirmation including, but limited to, a microscopic examination of brain tissue may be required for diagnosis. One skilled in the art would recognize that eight cognitive domains are most commonly impaired in patients suffering from a neurodegenerative disease (e.g., Alzheimer's disease): memory, language, perceptual skills, attention, constructive abilities, orientation, problem solving and functional abilities. These domains are equivalent to the NINCDS-ARDA Alzheimer's Criteria as listed in the *Diagnostic and Statistical Manual of Mental Disorders* (DSM-IV-TR) published by the American Psychiatric Association.

According to another aspect, the described invention provides a method for prolonging survival of a subject suffering from a neurodegenerative disease. It is understood that average life expectancy for patients suffering from a neurodegenerative disease (e.g., Alzheimer's disease) may vary between three (3) to ten (10) years following diagnosis.

According to another aspect, the described invention provides a kit comprising a composition, a means for administering the composition and a packaging material.

According to another aspect, the means for delivering the composition comprises syringe comprising the composition.

According to one embodiment, the composition of the kit is comprised of at least one EPO-derived peptide. According to another embodiment, the EPO-derived peptide is SEQ ID NO: 1. According to another embodiment, the composition of the kit further comprises a pharmaceutically acceptable excipient. According to yet another embodiment, the packaging material is an instruction.

According to one embodiment, the described invention provides a composition comprising at least one isolated, synthetic or substantially pure EPO-derived peptide.

Methods of isolating and purifying peptides are well-known in the art. The following procedures are exemplary of suitable isolation and purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns; or a specific antibody column to bind epitope-tagged forms of the protein of interest (e.g., nickel columns to bind His-tagged proteins, anti-HA columns to bind HA-tagged proteins, or anti-FLAG columns to bind FLAG-tagged proteins). Various methods of protein purification may be employed, and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular peptide produced.

The described invention provides synthetic peptides. Methods of preparing synthetic peptides are well-known in the art. See, e.g., *Peptide Synthesis Protocols*, Methods in Molecular Biology, vol. 35, Pennington, M. W. and Dunn, B. M., 1995, XII, Humana Press, Inc., Totowa, N. J. and *Peptides: Synthesis, Structures and Applications*, Gutte, B., 1995, Academic Press, Inc., San Diego, Calif. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained from Sigma, Cambridge Research Biochemical, or other chemical companies familiar to those skilled in the art. In addition, the peptides can be synthesized with other N-α-protecting groups that are familiar to those skilled in this art.

It is understood that the synthetic peptides may be from about two (2) to about thirty (30) amino acids in length. According to one embodiment, the described invention provides a synthetic peptide set forth in SEQ ID NO: 1 and its variants. The synthetic polypeptide variants can contain a substitution, deletion or addition of an amino acid. The substitution may include a conservative amino acid substitution. The deletion or addition may include a single amino acid or several amino acids.

It is understood that the described invention contemplates both linear and cyclic forms of EPO-derived peptides. According to one embodiment, the described invention provides a cyclic EPO-derived peptide. Cyclic peptides may be formed, for example, by an amide bond or disulfide bridge. A disulfide bridge may be formed between two residues of the amino acid cysteine. According to yet another embodiment, the described invention provides a cyclic EPO-derived peptide of the amino acid sequence set forth in SEQ ID NO: 1.

According to another embodiment, the described invention provides EPO-derived peptides that are non-hematopoietic. It is understood that non-hemapoietic peptides do not stimulate the formation of blood cells in a living body.

According to another embodiment, the described invention provides a route of administrating the composition. The composition may be constituted into any form suitable for the mode of administration selected. Exemplary routes of administration include, but are not limited to, parenteral (including subcutaneous), oral, inhalation, insufflation, topical, buccal and rectal. Compositions suitable for parenteral administration include sterile solutions, emulsions and suspensions. Oral administration include solid forms, such as pills, capsules, granules, tablets, and powders, and liquid forms, such as solutions, syrups, elixirs, and suspensions. Compositions suitable for inhalation and insufflation may take the form of an aerosolized solution. Compositions suitable for topical administration include creams, ointments and dermal patches. Compositions suitable for buccal administration may take the form of tablets or lozenges. Compositions suitable for rectal administration may take the form of suppositories. Formulations for administration may be provided using any formulation known in the art and appropriate for the route of administration. Such formulations may be as provided using the guidance of such resources as REMINGTON'S PHARMACEUTICAL SCIENCES, 18th ed., Mack Publishing Co., Easton, Pa. 1990.

According to another embodiment, the described invention provides for a composition comprising an EPO-derived peptide and a pharmaceutically acceptable excipient. Pharmaceutically acceptable excipients encompass any of the standard pharmaceutical carriers. For example, pharmaceutically acceptable excipients may include a solution that is isotonic with blood such as saline, Ringer's solution, or dextrose solution. Alternatively, non-aqueous vehicles such as fixed oils and ethyl oleate may be used, as well as liposomes. Further, excipients may be included that improve the efficacy, receptor affinity, or half-life of the active ingredient. For example, but not by way of limitation, the EPO-derived peptides of the methods of the described invention may be pegylated (i.e., coupled with polyethylene glycol) by means well-known in the art to prolong the half-life of the active ingredient in the circulation. (See, e.g., Kozlowski et al. J. Control Release 72: 217-224, 2001). Such modification may enhance biological activity to be useful as therapeutic agents.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis of Short, Stabilized EPO-Derived Peptide Library

EPO-derived peptides (ten (10)-twenty-five (25) amino acids) (SEQ ID NOs: X-Y) were synthesized and purified by commercial sources. Peptides were synthesized using Fmoc solid phase techniques on an automated peptide synthesizer using synthtic amino acids. Synthesized EPO-derived small peptides were purified by high performance liquid chromatography (HPLC) to more than 90% purity. Sample purity was established using MALDI-TOF mass spectrometry.

Example 2

Therapeutic Effect of Synthesized, Short, Stabilized EPO-derived Peptides in a Mouse Model of Chronic Neurodegenerative Disease In this study, tau mice (Jackson Laboratory) were used to test the therapeutic effect of the small EPO peptides on modifying the clinical and histopathologic outcome of a representative chronic neurodegenerative disease.

JM4 therapy was initiated in the tau mice (N=15) by administering 10 µg of JM4 subcutaneously for five (5) days per week after weaning early in the asymptomatic period at two (2) months of age. A control sham-treated group (N=22) was given phosphate-buffered saline (PBS). To determine the time of disease onset, animals were evaluated weekly by two observers (one of which was blinded). Disease onset was defined as mice exhibiting hindlimb grasping for more than 10 seconds or hindlimbs maintained in a retracted position for 30 seconds or longer when the animal was lifted by the tail. Animals were monitored until close to end of life (i.e., difficulty drinking/eating, limited mobility and onset of weight loss greater than 15%). This end of life point was used to develop Kaplan-Meier survival curves.

FIG. 1 shows the results of this study. Fourteen (14) out of the twenty-two (22) PBS-treated tau mice (open circles) suffered early onset of disease. Conversely, only five (5) out of the fifteen (15) JM4-treated tau mice (closed circles) showed evidence of emerging disease. Notably, JM4 delayed the onset of overt disease in the neurodegenerative tau model by approximately eighty (80) days (p=0.03).

Figure 2:
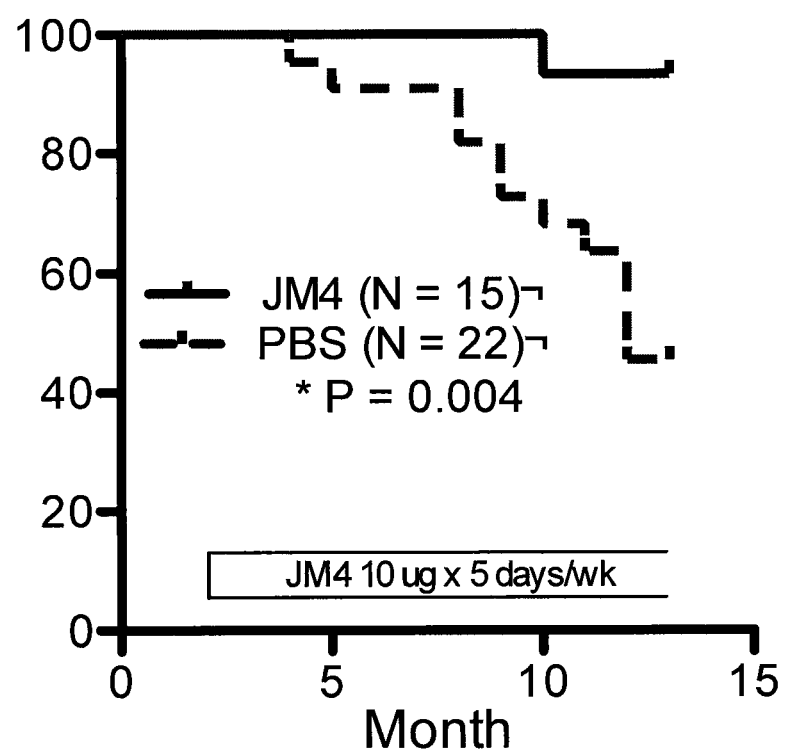
FIG. 2 depicts a Kaplan-Meier survival curve showing that JM4 is neuroprotective. JM4-treated tau mice (N=15) are depicted by a solid line. PBS-treated tau mice (N=22) are depicted by a dashed line (p=0.004).

In addition to delaying the onset of the neurodegenerative disease process, it was demonstrated that the JM4-treated tau mice showed a dramatic prolongation of life versus the PBS-treated group. FIG. 2 depicts a Kaplan-Meier survival curve showing that JM4 peptide is neuroprotective in tau mice when treatment was started early at two (2) months of age. Greater than 90% of the JM4-treated tau mice survived beyond one (1) year. In contrast, the PBS-treated tau mice survived poorly with less than 50% surviving after one (1) year (p=0.004).

Example 3

Neuropathology of JM4-treated Tau Mice Compared to PBS-Treated Tau Mice: Ventricular Size In this study, ventricular size of a normal mouse brain, a tau mouse brain treated with PBS and a tau mouse brain treated with JM4 was compared. Ventricles are known to grow larger as a result of Alzheimer's disease (de Leon et al., AJR 1989, vol. 152, no. 6, 1257-1262). The increase in ventricular size creates larger gaps in the brain and decreases overall brain mass resulting in mild cognitive impairment which is associated with the early stages of Alzheimer's disease.

Briefly, tau mice were subcutaneously administered 10 µg of JM4 or administered PBS five (5) days per week starting at two (2) months of age. Likewise, wild-type mice were subcutaneously administered PBS five (5) days per week starting at two (2) months of age. Mice were sacrificed, perfused with saline and the brains and spinal cords were placed in 4% parformaldehyde and embedded in paraffin. Paraffin-embedded brain and spinal cord were sectioned at five (5) microns and stained with hematoxylin and eosin for pathologic evaluation with particular reference to ventricular enlargement and hippocampal atrophy.

Figure 3:
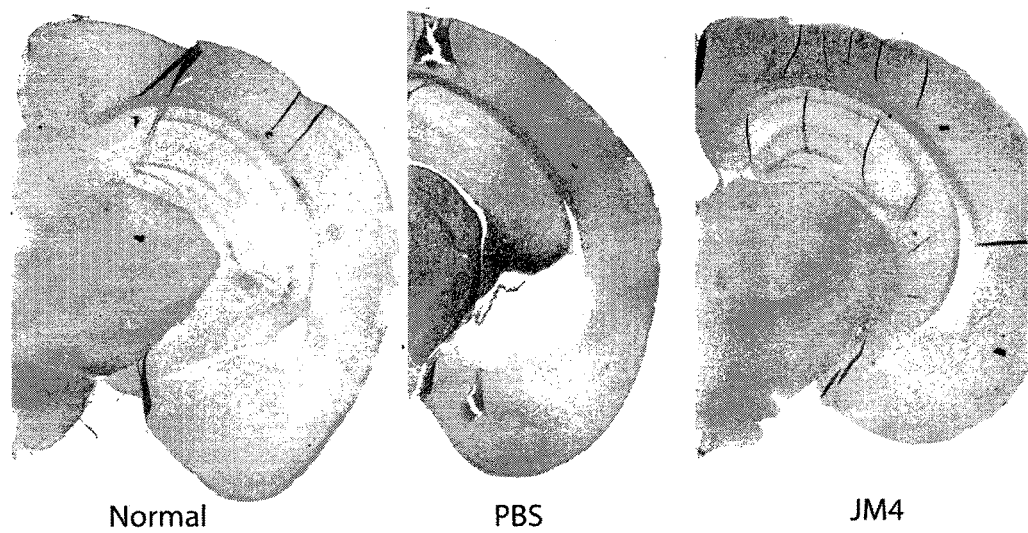
FIG. 3 depicts a comparison between ventricle size in normal mice and enlarged ventricle size in neurodegenerative tau mice. A brain section from a normal mouse is shown in the left panel. A brain section from a PBS-treated tau mouse is shown in the middle panel. A brain section from a JM4-treated tau mouse is shown in the right panel.

FIG. 3 shows the results of this study. The normal mouse (left panel) showed a small slit-like lateral ventricle. The PBS-treated tau mouse (middle panel) displayed substantial enlargement of ventricles as well as loss of brain volume. The tau mouse that was treated long-term with JM4 (right panel) displayed less loss of cortex and brainstem as well as reduced lateral ventricle size compared to the PBS-treated tau mouse.

Example 4

Neuropathology of JM4-treated Tau Mice Compared to PBS-Treated Tau Mice: Neurofilament Aggregates In this study, hippocampal sections from PBS-treated and JM4-treated tau/AD mouse brain were compared. Hippocampal sections were stained with an anti-phosphorylated tau antibody (AT8) to detect hyperphosphorylated neurofilament aggregates. The presence of neurofibrillary tangles in the brain is considered a hallmark characteristic of AD. Oxidative stress and activation of cell cycle regulators have been associated with neurofibrillary tangle formation (Nuomura et al., J. Neurosci. 1999, 19:1959-1964; Busser et al., J. Neurosci. 1998, 18:2801-2807). Tau protein contains a high content of lysine-serine-proline (KSP) domains. During oxidative stress, these KSP domains become phosphorylated through the activation of the MAP kinase pathway (Wataya et al., J. Biol. Chem. 2002, 277:4644-4648). It is phosphorylated tau protein that aggregates into paired helical filaments, which in turn, coalesce into neurofibrillary tangles in the AD brain.

Tau mice were subcutaneously administered 10 µg of JM4 or administered PBS five (5) days per week starting at 2 months of age. Mice were sacrificed and perfused with saline. After perfusion, the brains and spinal cords were removed and snap frozen. The frozen samples were then used for cryosectioning. The sections were assessed by immunohistochemistry for load of phosphorylated tau using AT8 antibody.

Figure 6:
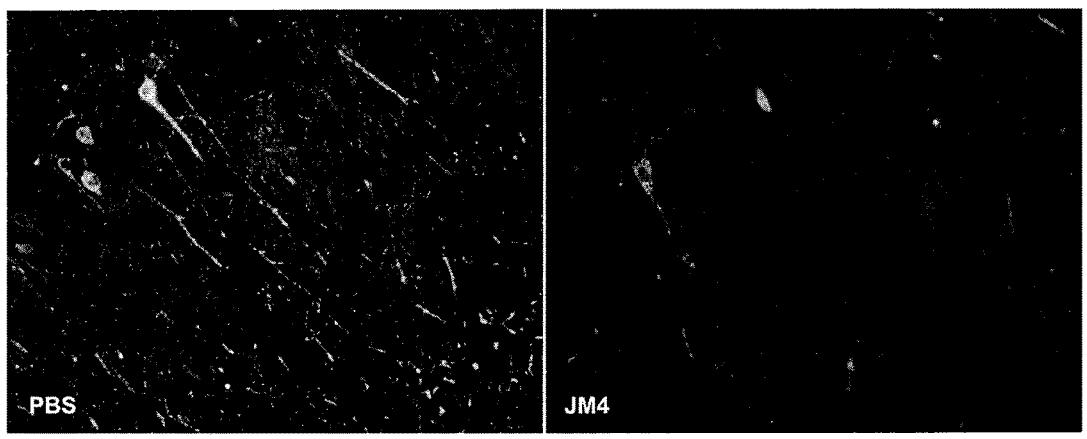
FIG. 6 shows a dramatic reduction in the burden of neurofilaments in JM4-treated (right panel) tau mouse brain using anti-phosphorylated tau antibody (AT8) on hippocampal sections when compared to a sham PBS-treated (left panel) tau model diseased control.

FIG. 6 shows the results of this study. The left panel shows abundant, strongly positive hyperphosphorylated neurofilament aggregates in hippocampal nerve cell bodies and their processes in a PBS-treated tau mouse brain. The right panel shows dramatically reduced neurofilament signal in a JM4-treated tau littermate after JM4 peptide therapy from age two (2) months to twelve (12) months. This data demonstrates the neuroprotective effect of JM4 protein in the neurodegenerative brain, and that JM4 markedly depleted the expected load of phosphorylated tau protein.

Example 5

Neuropathology of JM4-treated Tau Mice Compared to PBS-treated Tau Mice: MHC II Reactivity in Microglial Cells A study was performed in which major histocompatibility complex (MHC) II expression in PBS-treated and JM4-treated tau mouse brains was compared. MHC II is responsible for displaying degraded foreign proteins on the cell surface of macrophages for recognition by CD4+ T lymphocytes. In the brain, MHC II is expressed by microglia cells. Microglia cells are composed of mesodermally derived macrophages and function to support and protect nerurons. Increased MHC II gene expression was discovered in the hippocampus of AD cases with mild to moderate dementia and has been correlated with cognitive decline (Parachikova et al., Neurobiol. Aging 2007, 28:1821-1833; Tuppo et al., IJBCB 37 (2005) 289-305).

Tau mice were subcutaneously administered 10 µg of JM4 or administered PBS five (5) days per week starting at 2 months of age. Mice were sacrificed and perfused with saline. After perfusion, the brains and spinal cords were removed and snap frozen. The frozen samples were then used for cryosectioning. The cryosections were assessed by immunohistochemistry for MHC II expression.

Figure 7:
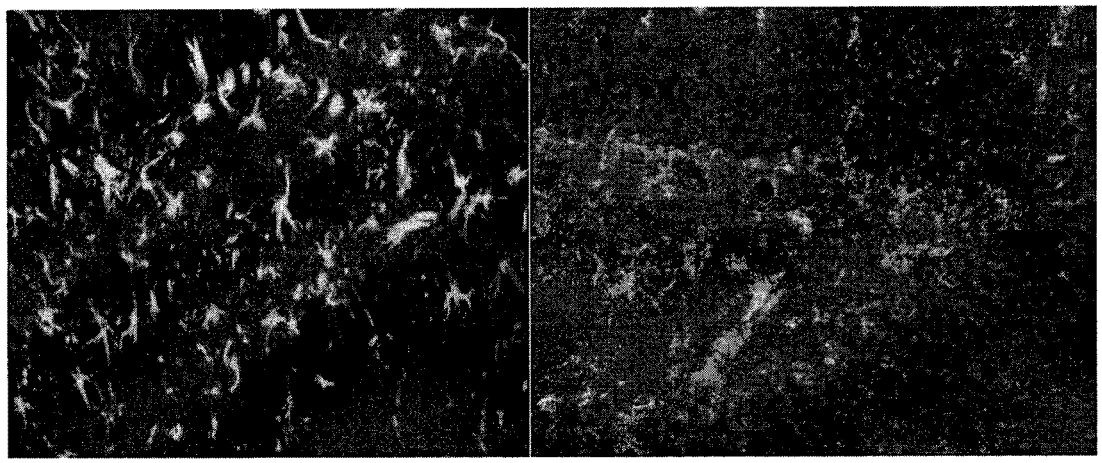
FIG. 7 shows that JM4 down-regulates microglial MHC II expression in cryosections of MHC II positive microglia in the hippocampal dentate gyrus of twelve (12) month old tau mice. The section in the left panel is of a tauopathy mouse treated with PBS. The section in the right panel is of a tau mouse treated long-term with JM4 (10 μg of JM4 subcutaneously for five (5) days per week).

FIG. 7 shows the results of this study. Increased MHC II expression was observed in the PBS-treated tau mouse hippocampus (left panel). In addition to increased MHC II expression, numerous reactive microglia with thickened appendages were apparent. There was also a reduced number of neurons seen in the neuronal layer (i.e., dentate gyrus) of the PBS-treated tau mouse as evidenced by a thin dark neuronal band. In contrast, MHC II expression was diminished in the JM4-treated tau mouse (right panel) hippocampus. Notably there was an increased number of neurons seen in the neuronal layer of the JM4-treated tau mouse as evidenced by the thick, dark neuronal band. This data demonstrates that JM4 normalized microglial MHC II expression (i.e., prevented overexpression of MHC II) in tau mice.

Example 6

Development of a Neurodegenerative Tau Mouse Model Containing a GFAP-luciferase Marker A neurodegenerative tau mouse model (GFAP-luc/tau mice) containing a glial fibrillary acidic protein (GFAP)-luciferase marker system was developed. GFAP is an intermediate filament protein predominantly expressed in cells of astroglial origin (i.e., astrocytes) within the central nervous system (CNS). Astrocytes are the most common cells in the brain and play a number of active roles, including brain-injury repair. During a response to brain injury (e.g., Alzheimer's disease), cytokines (e.g., transforming growth factor-beta1 and interleukin-1beta) activate astrocytes to elevate expression of GFAP. GFAP is used to fill the injured space by forming glial scar tissue as part of the healing process (Tuppo, E. E. and Arias, H. R., IJBCB 37 (2005) 289-305; Krohn, K et al., J. Neurochem. 1999 April; 72(4): 1353-1361). Thus, our GFAP-luc/tau mice emit bioluminescence when increased inflammation-induced GFAP synthesis occurs.

GFAP-luc/tau mice were created by crossing male GFAP-luc(+/−):C57 tyr− mice (Jackson Laboratory) with female strain129-Psen1$^{tm1Mpm}$ TG (APPSwe, tau P301L) 1Lfa/J mice (Jackson Laboratory) to generate Tg (129-Psen1$^{tm1Mpm}$ TG: GFAP-Luc) (i.e., GFAP-luc/tau) mice. Four (4) GFAP-luc/tau mice were treated with JM4 (10 ug 5 days/week, subcutaneus) from two (2) months of age. Four (4) additional GFAP-luc/tau mice were treated with PBS from two (2) months of age. The mice were followed monthly by measuring the strength of bioluminescent signal over diseased brain beginning at 2 months of age. Mice were administered D-luciferin (Xenogen) 15 mg/kg intraperitoneal injection (i.p.) and imaged 10 minutes after injection. The images were taken over a three (3)-minute period, three (3) animals at a time. The imaging signal was quantified using Xenogen LIVINGIMAGE software (version 3.0).

Figure 4:
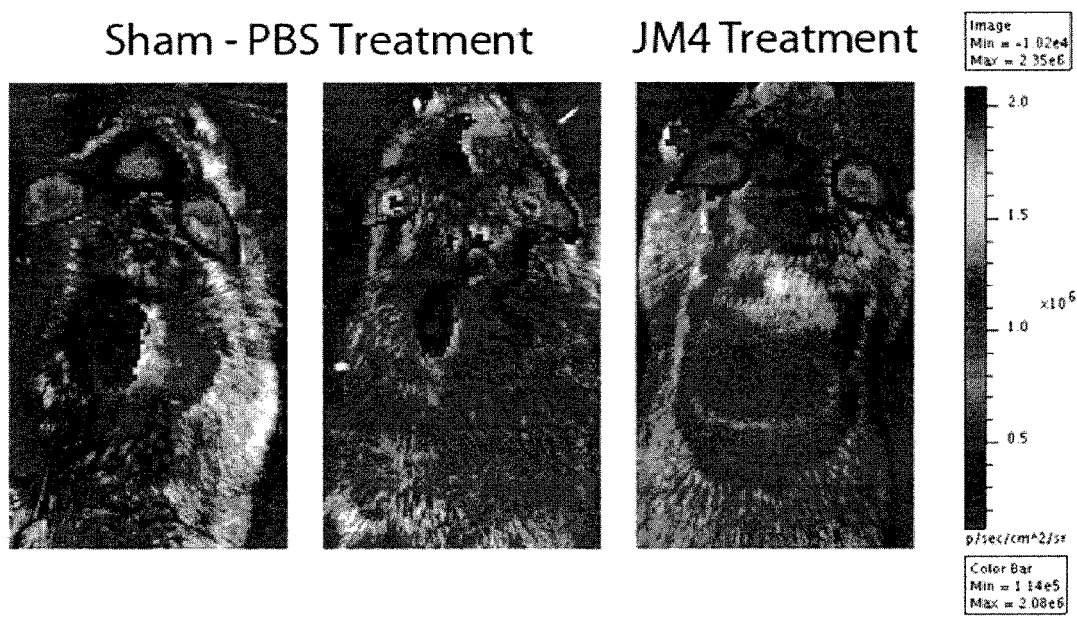
FIG. 4 illustrates the enhanced luciferase bioluminescence seen in aged late stage tau mice treated with JM4 long-term (right panel) compared to sham-treated with PBS (eleven (11) months old) (left and middle panels).

FIG. 4 illustrates luciferase bioluminescence in PBS-treated and JM4-treated GFAP-luc/tau mice. The PBS-treated GFAP-luc/tau mice (left and middle panels) initially developed signals restricted to the forebrain but after several months also developed spinal cord bioluminescence. The bioluminescence further increased as they became more symptomatic. The JM4-treated GFAP-luc/tau mouse (right panel) manifested little bioluminescence or signs of deficit until months later.

Figure 5:
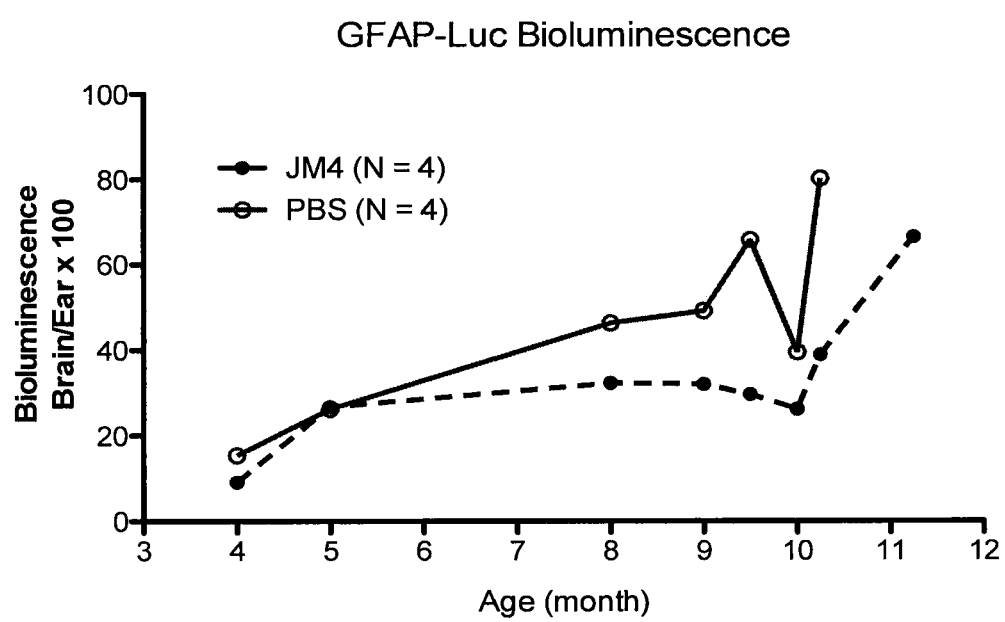
FIG. 5 is a graph showing that bioluminescence in JM4-treated GFAP-luc/tau mice was lower than in PBS-treated tau mice over time.

FIG. 5 shows a graph of monthly bioluminescence in four (4) JM4-treated GFAP-luc/tau mice and four (4) PBS-treated tau mice. The relative luminescence was the same at five (5) months for both groups. However, PBS-treated mice expressed higher levels of bioluminenscence than JM4-treated mice from five (5) months to eleven (11) months. At eleven (11) months, all four (4) PBS-treated animals failed to suvive whereas all four (4) JM4-treated mice survived beyond thirteen (13) months of age (data not shown).

GFAP-luc/AD mice were created by crossing male GFAP-luc(+/−):C57 tyr− mice (Jackson Laboratory) with female strain129-Psen1$^{tm1Mpm}$ TG (APPSwe, tau P301L) 1Lfa/J mice (Jackson Laboratory) to generate Tg (129-Psen1$^{tm1Mpm}$ TG: GFAP-Luc) (i.e., GFAP-luc/AD) mice (data not shown).

Example 7

Water Maze Testing of Long-term Memory in JM4-Treated AD Mice Compared to PBS-treated AD Mice The following water maze procedure was used to examine spatial reference memory (long-term memory) in triple transgenic AD mice treated subcutaneously with 10 μg of JM4 or with PBS five (5) days per week starting at 2 months of age. The water maze consisted of a pool (152 cm diameter) filled with water. Non-toxic paint was added to the water to hide a submerged escape platform, located 0.5 cm below the surface of the water. Six (6) trials were given in a session and one (1) session per day for a total of three (3) days. On each trial, a AD mouse was put into the water facing the outer edge of the pool. The mouse was allowed to search for the escape platform for sixty (60) seconds. If the mouse found the platform, it was allowed to remain on the platform for fifteen (15) seconds and then removed and put into a holding cage for thirty (30) seconds. If the mouse was unable to find the platform after sixty (60) seconds, it was led to the platform by the experimenter and allowed to remain on the platform for fifteen (15) seconds before being dried and placed into the holding cage. On each of the six (6) trials, the mouse was started from a different randomized location. The order of the starting locations was varied across sessions. Latency to reach the platform was recorded and analyzed. Following the three (3) days of training, a probe procedure was performed to assess how well the mice remembered the location of the escape platform. This probe procedure was performed twenty-four (24) hours following the previous training session. For the probe trial, the escape platform was removed and the mouse was allowed to swim for sixty (60) seconds. The probe trial was completely documented by videotape. Measures of performance on probe trials consisted of the time spent in the target quadrant (i.e., where the platform previously was located), time spent near the platform location, and number of times the mouse crossed over the platform location.

Figure 8:
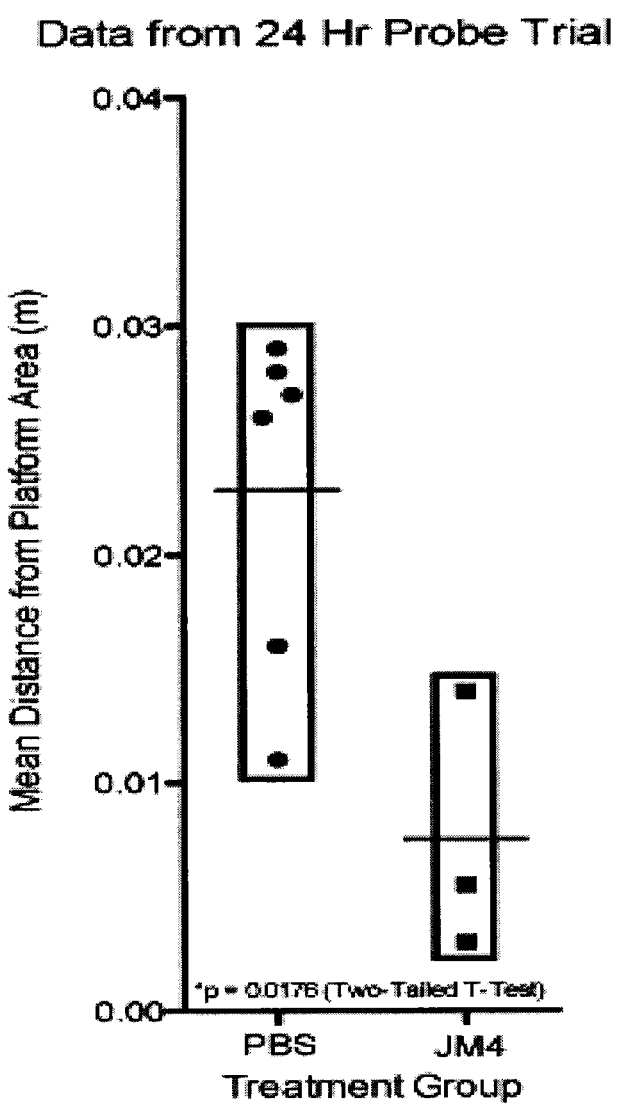
FIG. 8 shows that JM4-treated mice have limited cognitive impairment when compared to PBS-treated mice. Water maze testing was performed on aged (17 month old) triple transgenic AD mice treated long-term with JM4 (squares) or with PBS (circles).

FIG. 8 depicts the results of this experiment. JM4-treated triple transgenic AD mice at 17 months of age demonstrated limited cognitive impairment when compared with PBS-treated AD mice. The JM4 treated AD group showed a search pattern that was significantly closer to the area of the platform than that seen in PBS-treated mice (p=0.009).

Methods

Tissue Preparation

After perfusion with saline, mouse brains and spinal cords were removed and snap frozen. The frozen samples were used for cryosectioning. The sections were routinely assessed by immunohistochemistry for load of phosphorylated tau (AT8), degree of synaptic loss (synaptophysin antibody), MHC II overexpression colocalized with Iba-1 for microglia and GFAP for astrocytes [21]. The degree of neuronal dropout was quantified by counting the number of hippocampal cell bodies in the representative areas from CA1 and CA3 as described by Yoshiyama et al. (J. Alz. Dis. 2010, 22: 295-306).

Immunohistochemistry

Routine neuropathological evaluation of sections were conducted with hematoxylin and eosin (H&E) and Luxol Fast Blue. Neural types and expression levels were characterized by antibodies specific for phosphorylated tau (AT8), synaptophysin, syntaxin, the cytokines IL-β and COX2, GFAP (astrocyte), Iba-1, CD11c, CD11b, Lectin (macrophage/microglia), MHC II and for triple transgenic AD animals APP and beta amyloid products (6E10). Controls for immunocytochemistry included preimmune serum when available, omission of the primary antibody, antibody replacement with normal serum, and subclass-specific negative serum. Preferably, chromogen diaminobenzidine (DAB) conjugated with horseradish peroxidase (HRP) (brown staining) and no counterstain was used.

In many applications, immunofluorescent detection was used. Multi-label immunofluorescent staining enhances the distinction between labels and backround stain more clearly than peroxidase/alkaline phosphatase co-localization. We routinely used numerous secondary antibody detection systems conjugated with fluorophores. Such fluorphores included, for example, Cy2, Cy3, 488, AMCA, Texas red and FITC. A four-channel Zeiss confocal microscope and deconvolution microscope were used for the final co-localization studies. The Tyramide Signal Amplification (TSA) detection system is highly effective in detecting weak signals.

Animal Breeding

The DNA from both C3-Tg (Prnp-MAPT*P301S) PS19Vie/J Tauopathy Model (Jackson Laboratories) and 129-Psen1$^{tm1Mpm}$ TG (APPSwe, tau P301L) 1Lfa/J mouse strain (Jackson Laboratories) was characterized from tail snips by Jackson Laboratories and reconfirmed by in house PCR.

1. 129-Psen1$^{tm1Mpm}$ TG: GFAP-Luc

In house male GFAP-luc(+/−):C57 tyr− strain* will be crossed with female strain129-Psen1$^{tm1Mpm}$ TG (APPSwe, tau P301L) 1Lfa/J mice to generate Tg (129-Psen1$^{tm1Mpm}$ TG: GFAP-Luc) colony of animals. Paternal GFAP-luc (+/−):C57 tyr− is heterozygous, maternal strain129-Psen1$^{tm1Mpm}$ TG is homozygous. The probability of having heterozygote offspring is 50%.

2. C3-Tg Prnp-MAPT*P301S:GFAP-Luc

Male GFAP-luc(+/−):C57 tyr− strain* will be crossed with the female strain C3-Tg (Prnp-MAPT*P301S) PS19Vle/J to generate Tg (C3-Tg (Prnp-MAPT*P301S): GFAP-Luc mice. Paternal GFAP-luc(+/−):C57 tyr− is heterozygous, maternal strain C3-Tg (Prnp-MAPT*P301S) is also heterozygous. The probability of having a heterozygote offspring is 25%. Study enrollment was made upon confirmation of genotype. Both genders of heterozygote offspring were selected for study based on tail snip genotyping results. (Jackson Laboratories genotyping protocol was followed). The correct genotypes were 129-Psen1$^{tm1Mpm}$ TG (+/−): GFAP-Luc(+/−) and C3-Tg Prnp-MAPT*P301S (+/):GFAP-Luc(+/−).

* GFAP-luc(+/−):C57 tyr was obtained by crossing the commercially available FVB/N-Tg(Gfap-luc)-Xen (Caliper, Hopkinton, Mass.) with the C57BL/6J-Try$^{c-2J}$ strain (Jackson Laboratory).

PCR Screening of GFAP-Luciferase Positive Mice

Tails from F1 offspring of GFAP-luc(+/−):C57 tyr (containing the GFAP-luciferase gene) crossed with C3-Tg (Prnp-MAPT*P301S) PS19Vie/J Tauopathy Model or 129-Psen1$^{tm1Mpm}$ TG (APPSwe, tau P301L) 1Lfa/J mouse strain were digested in a solution of 25 mM NaOH/0.2 mM EDTA for one (1) hour at 95° C., and then neutralized with 40 mM Tris solution. One (1) μl of this solution was then used for a PCR reaction with the HotstarTaq Master Mix Kit (Qiagen). A 600 base-pair (bp) PCR product from internal sequence coding for the luciferase gene was amplified using the following forward and reverse primers: 5'-GAAATGTC-CGTTCGGCAGAAGC-3' (SEQ ID NO: 2) and 5'-CCAAAACCGTGATGGAATGGAACAACA-3' (SEQ ID NO: 3), respectively. Both primers were maintained at a concentration of 0.4 μM in the reaction mix. The PCR conditions used were 95° C. for 15 min, 94° C. for 30 seconds, 65° C. for 30 seconds, and 72° C. for one (1) minute for thirty (30) cycles. The product was characterized in a 1% agarose gel electrophoretic step.

Two-step real-time PCR was performed by an ABI 7700 Sequence Detection System (PE Applied Biosystems, Foster City, Calif., USA) using SYBR-Green I Master (Roche Diagnostics, Indianapolis, Ind., USA). First, cDNA was synthesized using SuperScript VILO (Invitrogen) on 2 μg of total RNA extracted with Trizol (Invitrogen) according to the manufacturer's protocol. Two (2) μl of 20 times-diluted RT-PCR reaction solution was used for the real-time PCR reaction. Primers for amplifying the GFAP product were 5'-ATGGTGATGCGGTTTTCTCTTC-3' (SEQ ID NO: 4) and 5'-CACGAACGAGTCCCTAGAGC-3' (SEQ ID NO: 5). Primers for amplifying the luciferase product were 5'-GCTTTTGGCGAAGAATGAAA-3' (SEQ ID NO: 6) and 5'-CATTCCGCATACTGAGATTT-3' (SEQ ID NO: 7). The real-time PCR conditions utilized were: 94° C. for 25 seconds, 60° C. for 25 seconds, and 72° C. for 45 seconds for forty (40) cycles. Quantification was performed using the relative standard curve method described in User Bulletin #2 by PE Applied Biosystems. Hypoxanthine guanine phosphoribosyl transferase 1 (HPRT1) was used as an endogenous control. Standard curves were generated using six (6) serial dilutions A correlation score of >0.99 was observed for each run. Each sample was run in triplicate, and the average Ct value was used for analysis. The melting temperature was studied with a dissociation curve, and a 1% agarose gel was run to verify the PCR products.

Statistical Analysis on Digital Imaging Results

Our facility for confocal and light microscopy is connected to digital imaging software (ONCOR and IP 4.0). Counting of hippocampal neurons in the CA1/CA3 region was performed using an indexing grid of 1 mm square. We quantified the hippocampal cells for statistical analysis by having three observers count the neural cells per mm square first by light microscopy and then independently by confocal microscopy. The degree of significance depended upon the number of sections and the number of quantifiable cells per grid. Comparison of data within and between control groups was performed by the Kruskal-Wallis and Mann-Whitney U tests. The data was transformed where appropriate, in compliance with the assumptions of the statistical models. For analysis of onset of disease and Kaplan-Meier data, univairate and multivariate analyses were performed with adjustments for multiple comparisons.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A kit comprising a composition comprising a cyclic EPO-derived peptide of SEQ ID NO: 1.

2. The kit according to claim 1, wherein the composition further comprises a pharmaceutically acceptable excipient.

* * * * *

SEQUENCE LISTING

<160> NUMBER OF SEQ ID NOS: 7

<210> SEQ ID NO 1
<211> LENGTH: 19
<212> TYPE: PRT
<213> ORGANISM: Homo sapiens

<400> SEQUENCE: 1

Gly Cys Ala Glu His Cys Ser Leu Asn Glu Asn Ile Thr Val Pro Asp
1               5                   10                  15

Thr Lys Val

<210> SEQ ID NO 2
<211> LENGTH: 22
<212> TYPE: DNA
<213> ORGANISM: Artificial
<220> FEATURE:
<223> OTHER INFORMATION: Primer

<400> SEQUENCE: 2
gaaatgtccg ttcggcagaa gc                                         22

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
ccaaaaccgt gatggaatgg aacaaca                                    27

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
atggtgatgc ggttttctct tc                                         22

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
cacgaacgag tccctagagc                                            20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
gcttttggcg aagaatgaaa                                            20

<210> SEQ ID NO 7
<211> LENGTH: 20
<212> TYPE: DNA

```
<213> ORGANISM: Artificial
<220> FEATURE:
<223> OTHER INFORMATION: Primer

<400> SEQUENCE: 7
cattccgcat actgagattt                                          20
```